(12) United States Patent
VanDer Meulen et al.

(10) Patent No.: US 7,819,924 B2
(45) Date of Patent: Oct. 26, 2010

(54) DISTAL RADIOULNAR JOINT PROSTHESIS

(75) Inventors: Steve VanDer Meulen, Leander, TX (US); Robert Martin, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 477 days.

(21) Appl. No.: 11/558,822

(22) Filed: Nov. 10, 2006

(65) Prior Publication Data

US 2007/0198095 A1 Aug. 23, 2007

Related U.S. Application Data

(60) Provisional application No. 60/736,658, filed on Nov. 14, 2005.

(51) Int. Cl.
*A61F 2/42* (2006.01)
(52) U.S. Cl. .................................. 623/21.11; 623/21.12
(58) Field of Classification Search .............. 623/16.11, 623/18.11, 12.11, 21.12, 21.13, 23.11, 23.35, 623/23.42, 23.47, FOR. 112, FOR. 117, 21.11; *A61F 2/42*
See application file for complete search history.

(56) References Cited

U.S. PATENT DOCUMENTS

| | | |
|---|---|---|
| 4,180,871 A | 1/1980 | Hamas |
| 4,784,661 A | 11/1988 | Beckenbaugh et al. |
| 5,549,609 A | 8/1996 | Frankel et al. |
| 5,779,709 A | 7/1998 | Harris, Jr. et al. |
| 5,906,210 A | 5/1999 | Herbert |
| 5,938,699 A | 8/1999 | Campbell |
| 5,951,604 A | 9/1999 | Scheker |
| 6,059,832 A | 5/2000 | Menon |

(Continued)

FOREIGN PATENT DOCUMENTS

GB 2269752 2/1994

OTHER PUBLICATIONS

Sauerbier M et al., Analysis of Dynamic Distal Radioulnar Convergence After Ulnar Head Resection and Endoprosthesis Implantation, 2002, Churchill Livingstone, vol. 27 issue 3, p. 425-34.*

(Continued)

*Primary Examiner*—William H. Matthews
*Assistant Examiner*—Marcia Hoffman
(74) *Attorney, Agent, or Firm*—Fitch, Even, Tabin & Flannery

(57) ABSTRACT

A prosthetic implant for partial resurfacing of the ulna at the distal radioulnar (DRU) joint which comprises a stem and an ulnar head. The combination of the anchoring stem and the head that is shaped and proportioned to replace only a portion of the distal ulnar head and the radial articulating surface and to interface with the resected ulna at a proximal stabilizing surface provides excellent stability in the completed implant. In the preferred embodiment, a pair of strategically located surfaces aligned at an obtuse angle provides the stabilizing surface arrangement. The provision of a set of such implants with different head and stem sizes allows a surgeon to best accommodate the physiology of a particular patient and locate a resurfaced head section offset from the canal center in order to provide a convex articular surface adjacent the radius which will allow the radius to smoothly pivot and translate around such resurfaced ulnar head during pivoting of the forearm.

10 Claims, 5 Drawing Sheets

U.S. PATENT DOCUMENTS

| | | | |
|---|---|---|---|
| 6,302,915 | B1 | 10/2001 | Clooney, III et al. |
| 6,459,948 | B1 | 10/2002 | Ateshian et al. |
| 6,814,757 | B2 | 11/2004 | Kopylov et al. |
| 6,945,976 | B2 | 9/2005 | Ball et al. |
| 7,160,331 | B2 | 1/2007 | Cooney, III et al. |
| 2001/0021876 | A1 | 9/2001 | Terrill-Grisoni et al. |
| 2004/0186580 | A1 | 9/2004 | Steinmann |
| 2005/0049710 | A1 | 3/2005 | O'Driscoll |
| 2006/0069445 | A1* | 3/2006 | Ondrla et al. ............ 623/19.12 |

OTHER PUBLICATIONS

Gordon et al., Kinematics of Ulnar Head Arthroplasty, 2003, Journal of Hand Surgery (Birtish and European Volume), vol. 28B:6, p. 551-58.*

Masaoka et al., Biomechanical Analysis of Two Ulnar Head Prostheses, 2002, Journal of Hand Surgery, Churchill Livingstone, Sept:27(5), p. 845-53.*

Fornaiski et al. "Chronic Instability of the Distal Radioulnar Joint: A Review", University of California, Urvine, Department of Orthopedic Surgery Spring 2000 vol. 13, PDF p. 13-15.*

* cited by examiner

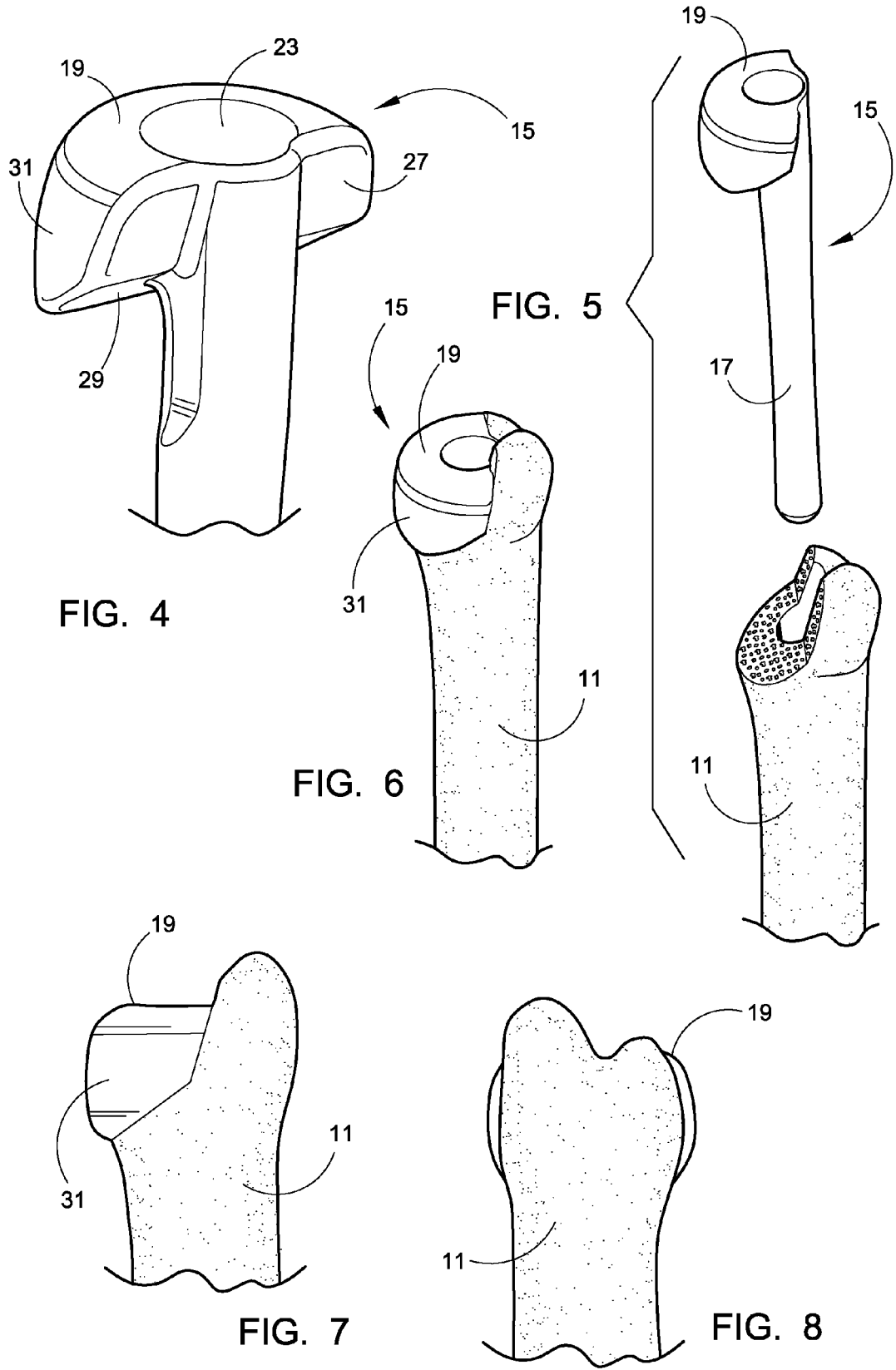

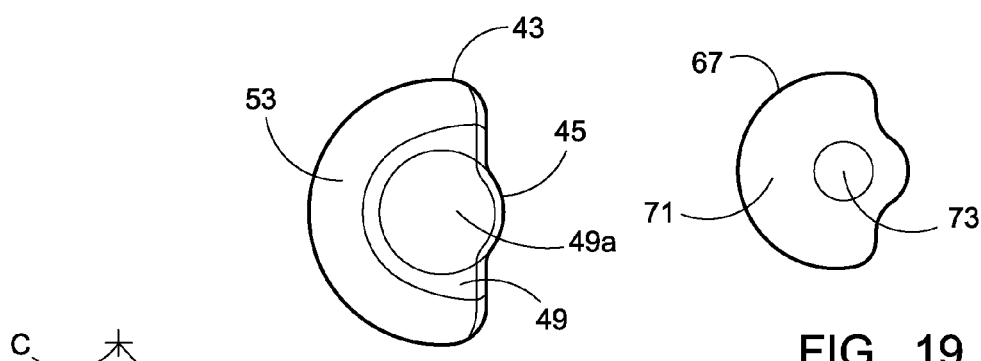
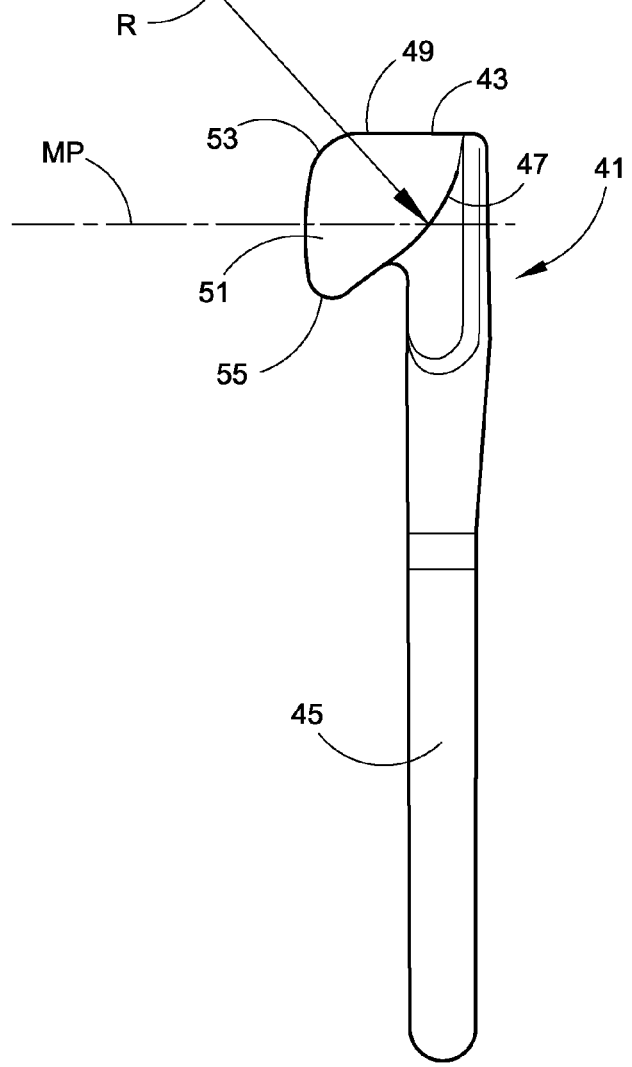
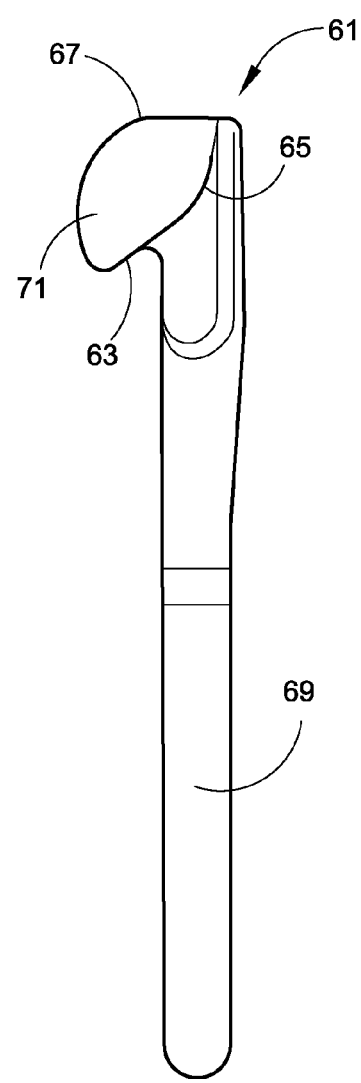
FIG. 17
FIG. 19
FIG. 16
FIG. 18

DISTAL RADIOULNAR JOINT PROSTHESIS

This application claims priority from U.S. provisional application No. 60/736,658 filed Nov. 14, 2005.

FIELD OF THE INVENTION

This invention relates to a joint prosthesis, and more particularly to a partial replacement for the ulna at the distal radioulnar (DRU) joint of the forearm.

BACKGROUND OF THE INVENTION

Cartilage destruction of the distal radioulnar joint is often caused by disease, such as different types of rheumatoid diseases, especially rheumatoid arthritis. Today these injuries are operated rather late in the evolution of the disease when pain evolves or mobility starts to decrease. At this time the joint most often is destroyed without remaining cartilage and with varying degrees of bone destruction. A common operation often used is the Darrach procedure, which consists of a simple resection of the ulnar head (caput ulna). The cut ulnar bone-end is now mobile and "floats" and sometimes the wrist feels unstable and painful. There is a risk for the ulna and radius to stick to each other. Sometimes the patient feels a clicking sensation, sometimes painful, when turning the forearm. Another consequence of rheumatoid arthritis is a destruction of the ligaments, joint capsule or other connective tissues stabilizers crossing the DRU joint. A tear or weakening of these structures such as the distal radioulnar ligaments and the interosseus membrane, as a result of rheumatoid diseases can compromise the stability of the DRU joint because of the loss of tension in the radioulnar ligaments. This loss of ligament tension may allow the DRU joint to sublux or dislocate.

In the non-rheumatoid patients, the DRU joint most often is injured as a consequence of a distal radial fracture and/or any distal radioulnar ligaments or interosseus membrane tear, causing a secondary joint surface incongruity or instability of the distal radial ulnar joint. The incongruity may also occur as a consequence of an intraarticular radial fracture extending into the DRU joint. The joint surface then heals with a step-off. Also a radial fracture, which does not extend into the DRU joint, might influence the congruity due to an angulation of the radial shaft and the radial joint surface of the DRU joint. A distal radioulnar ligament tear might compromise the stability of the DRU joint as a consequence of loss of tension in the radioulnar ligaments or interosseus membrane. This loss of ligament tension may allow the DRU joint to sublux or dislocate.

The consequence of an incongruity may be an osteoarthritis, which might be either symptomatic or not. Different treatment alternatives exist, none of them being particularly good. All are compromises, trading different wrist and hand functions to achieve pain relief. A common method is the Sauvee-Kapandjii procedure, where the ligaments from the ulnar tip to the radius and carpus are maintained, the ulna is resected proximally and screws keep the ulnar head to the radius. The radius together with the ulnar head now pivot within the osteotomy defect. Other known methods comprise the Bowers hemiresection of the ulnar end with soft tissue interposition and the Watson distal ulnar resection. Methods to resect the ulnar head and replace it with a prosthesis are also described; see for example, U.S. Pat. Nos. 5,951,604 and 6,302,915 and published international application No. WO 2004/071357.

U.S. Pat. No. 6,814,757 to Kopylov et al. teaches the use of implants to resurface the articular surface(s) of the distal portion(s) of radius and/or ulna bone(s) that form the DRU joint without meaningfully disturbing either the ligaments or their attachment sites that stabilize the DRU joint so as to keep the DRU joint as intact as possible.

Although the '757 patent system provides an effective treatment system, in the orthopedics industry, there is a constant search for improvement.

SUMMARY OF THE INVENTION

The present invention provides an improved implant that may be used when only the articular surface of the ulna has deteriorated. A set of such implants are preferably designed and provided so as to allow adjustment of the tension upon the DRU ligament through selection of prosthesis of appropriate head size, offset and stem size. Stated another way, the invention provides a prosthesis for effectively resurfacing the distal lateral region and a portion of the head of the ulna at the site of articular cartilage in a physiologic DRU joint, which region articulates against the ulnar notch of the radius.

Generally, the invention provides a prosthesis for partial replacement of the ulnar head at the distal radioulnar joint, which implant comprises a stem designed to fit within a bore created in a patient's ulna and a head which has a preferably double-curved articular surface and a stabilizing surface arrangement that interfaces with the resected ulna and provides for stable replacement of the radial-articulating surface of the distal ulna. The preferred interfacing surface arrangement includes a pair of planar surfaces aligned at an obtuse angle to each other.

In one particular aspect, the invention provides a prosthetic implant for partial replacement of the ulnar head at the distal radioulnar joint (DRUJ) without disturbing attachment of ulnal carpal ligaments and the triangular fibrocartilaginous complex (TFCC), which implant comprises a stem designed to fit within a bore created in a patient's ulna and a head which surmounts said stem and is proportioned to replace the radial-articulating surface of the distal ulna and only a portion of the ulnar head, which portion extends past the centerline of the medullary canal, said implant head having a double-curved lateral articular surface and a distal stabilizing surface from which said stem extends, which distal surface stably interfaces with a complementary surface of the resected ulna of the DRUJ when implanted.

In another particular aspect, the invention provides a prosthetic implant for partial replacement of the ulnar head at the distal radioulnar joint (DRUJ), which implant comprises a stem designed to fit within a bore created in a patient's ulna and a head which has a double-curved articular surface and a pair of planar stabilizing surfaces located at an obtuse angle to each other whereby the implanted prosthesis provides for stable replacement of the radial-articulating surface of the distal ulna without disturbing attachment of ulnal carpal ligaments and the triangular fibrocartilaginous complex (TFCC).

In a further particular aspect, the invention provides a method of repairing a distal radial ulna joint (DRUJ), which method comprises the steps of providing a prosthetic implant which includes a head that surmounts a stem that is proportioned to be received in the medullary canal of the ulna of a patient, which head is proportioned to replace the radial-articulating surface of the distal ulna and only a portion of the ulna head, which portion extends past the centerline of the medullary canal, and which head has a proximal stabilizing surface which is contiguous at the distal end of said stem, treating the distal end of the ulna of the patient to provide an opening to the medullary canal, reaming the canal to the desired size to accommodate the implant stem and resecting the portion of the ulnar head facing the radius to shape the ulnar head with a surface that is complementary with the proximal stabilizing surface of the implant head, and fully inserting the stem of the implant into the reamed canal to accomplish a tight press fit, with the stabilizing surface of the head physically abutting the resected surface of the ulnar head of the patient, which steps are carried out without disturbing attachment of ulnal carpal ligaments and the triangular fibrocartilaginous complex (TFCC).

BRIEF DESCRIPTION OF THE DRAWINGS

FIG. 4 is a fragmentary perspective view of a prosthesis embodying various features of the present invention.

FIG. 5 is an exploded perspective view showing the prosthesis of FIG. 4 and the reamed and resected ulna of FIG. 3.

FIG. 6 is a perspective view showing the prosthesis and the ulna of FIG. 5 after implantation.

FIG. 7 is a fragmentary front or dorsal view of FIG. 6.

FIG. 8 is a side view of the repaired ulna of FIG. 6.

FIG. 16 is a left side view of an alternative embodiment of a prosthetic implant embodying various features of the invention.

FIG. 17 is a top view of the distal surface of the implant of FIG. 16.

FIG. 18 is a left side view of another alternative embodiment of a prosthetic implant embodying various features of the invention.

FIG. 19 is a top view of the distal surface of the implant of FIG. 18.

DETAILED DESCRIPTION OF THE PREFERRED EMBODIMENTS

Figure 1:
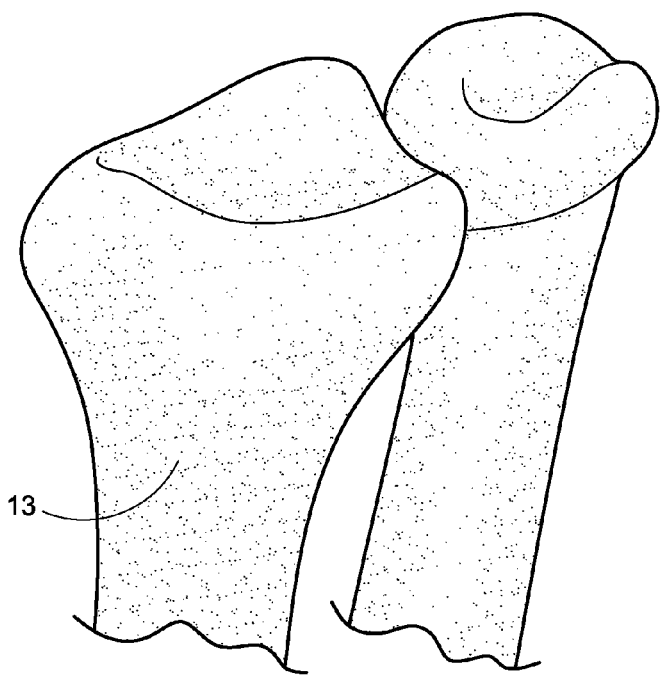
FIG. 1 is a schematic perspective view showing a normal DRU joint.

The invention provides a prosthesis which can be implanted, for example, after a fracture, rheumatoid arthritis or other rheumatoid disease involving the distal radioulnar joint. The motion, which is supported by the use of the implant, is the turning (pronation/supination) of the forearm. The ulna 11 is the non-moving and weight-bearing fundament of the DRU joint (see FIG. 1), while the radius 13 is a mobile component with mostly compressing forces influencing the positioning during the turning movement. The radius 13 turns around the ulnar head. In addition to the distal joint surfaces between the radius and ulna, a prerequisite for turning movement is the existence of joint surfaces proximally in the elbow, and the proximal radioulnar joint consists of the radial head and the ulna with a fossa radii and an annular ligament.

At the elbow, the ulna 11 makes a flexion or extension motion, whereas the radius 13 rotates around it own axis. Both the radius and the ulna have curvatures that such the middle points of the two bones are located relatively far away from each other. As a result of such arrangement, the radius has enough space to be able to rotate around the ulna.

Stability depends on the congruity of the two radioulnar joints as well as upon the ligaments of the two joints keeping the radius and ulna together. Muscle forces push the two bones together, while still allowing them to execute both rolling and translatory motion relative each other. The forces in the DRU joint thus are mainly compressive. Different parts of the ulnar head will be in contact with the articular surface of the radius at the joint as the ulnar head successively translates and rotates along the radial surface. In the two extreme positions of pronation and supination, the articular surface of the radius is loaded at the volar part and the dorsal part respectively. The DRU joint ligaments stop the joint from luxation, and the joint is secondarily stabilized by the interosseus membrane When problems arise in the DRU joint, it has been common, as previously mentioned, to simply resect the entire ulnar head and either attach it to the radius or replace it with a prosthesis. The result of this is that the distal position of the radius often becomes changed because the radius 13 is resting upon the ulna 11. Such a change of position may make the result of the operation less satisfactory.

By only partial surface replacement, which is accomplished by implanting a prosthesis 15 according to the present invention or a component as taught in the '757 patent, the ulna 11 is kept substantially intact, and it is thus able to support the radius 13 without changing the position of the radius in any nonfavorable way. Moreover, use of prostheses having features of the invention also makes it possible to preserve the significant parts of the ligamentous apparatus when implanting the surface replacement. This means that the compressive forces within the DRU joint are maintained after the operation and contribute to the stabilization of the joint. Moreover, if a surgeon is able to select the appropriate size implant, preferably from a set of 12 different sizes, the surgeon is able to select the very best fit once the ulna has been resected which will allow him to provide a smooth interface with the articular surface of the radius and get a stable DRU joint.

The implant 15 accomplishes effective partial surface replacement in a particularly stable manner through the use of an integral body having an intramedullary stem 17 and an integral head 19 that replaces only a portion of the distal head and the contiguous ulna surface component facing the head of the radius. The stem 17 enhances the initial stability of the implant to lateral forces and torques that will be experienced about the long axis of the ulna 11. Because the stem 17 is shaped to require only minimal resection of the radial side of the distal ulna, major portions of the soft tissue stabilizing structures which cross the DRU joint are preserved, such as the triangular fibrous cartilage complex (TFCC) and the radioulnar ligaments. The TFCC bridges between the distal radius and ulna; the TFCC originates along the ulnar edge of the radius, and becomes an extension of the distal radius articular surface. The distal cartilage pad of the TFCC articulates against the lunate and triquetrum. On the ulna 11, the TFCC originates from the fovea and radial side of the ulna. The volar and dorsal radioulnar ligaments run along the volar and dorsal edges of the TFCC, respectively, and connect the radius 13 to the ulna. This complex of soft tissue structures adds form to DRU joint and assists controlling the position of the radius 13 relative to the ulna 11 during use, such as during pronation-supination of the forearm and flexion-extension of the wrist.

The stem 17 of the prosthesis 15 can be inserted without disturbing the structural integrity of the ulna styloid and while the majority of the attachments of the TFCC on the radial aspect of the styloid also remain undisturbed. The length and shape of the stem 17 are selected to allow it to pass into the medullary canal without creating excessive lateral pressure on the styloid. The provision of an outward taper 21 on the stem further stabilizes it within the reamed passageway in the intermedullary canal.

It has been found that the location of the prosthesis head that provides the best fit for a repaired articular region of the ulna head of a particular patient will vary, from patient to patient, relative to the centerline of the long axis of the ulna medullary canal, i.e. the canal centerline or axis. Thus, in order to accommodate such anthropometeric variations, it is preferable that a set of prostheses 15 is provided, with varying head sizes and offsets, from which the surgeon can select, once reaming and resection have taken place. Such an arrangement will allow the surgeon to both properly fit the head diameter to the size of the ulna notch of the radius, tension the stabilizing soft tissues, such as the TFCC, which cross the DRU joint, and select the best fitting stem size.

Figures 13, 14, 15:
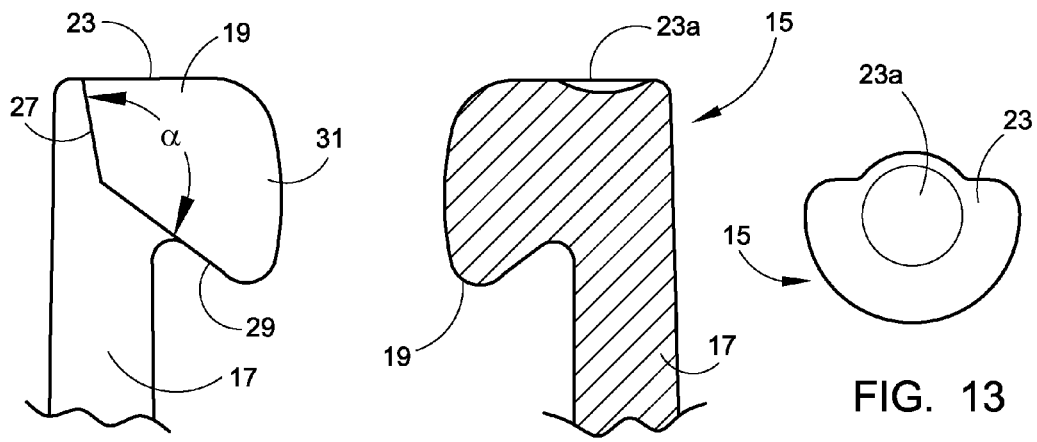
FIG. 13 is a top view of the distal surface of the prosthesis of FIG. 12.
FIG. 14 is a fragmentary view similar to FIG. 11 without the blend lines showing changes in curvature.
FIG. 15 is a fragmentary sectional view taken along line 15-15 of FIG. 12.
Figures 11, 12:
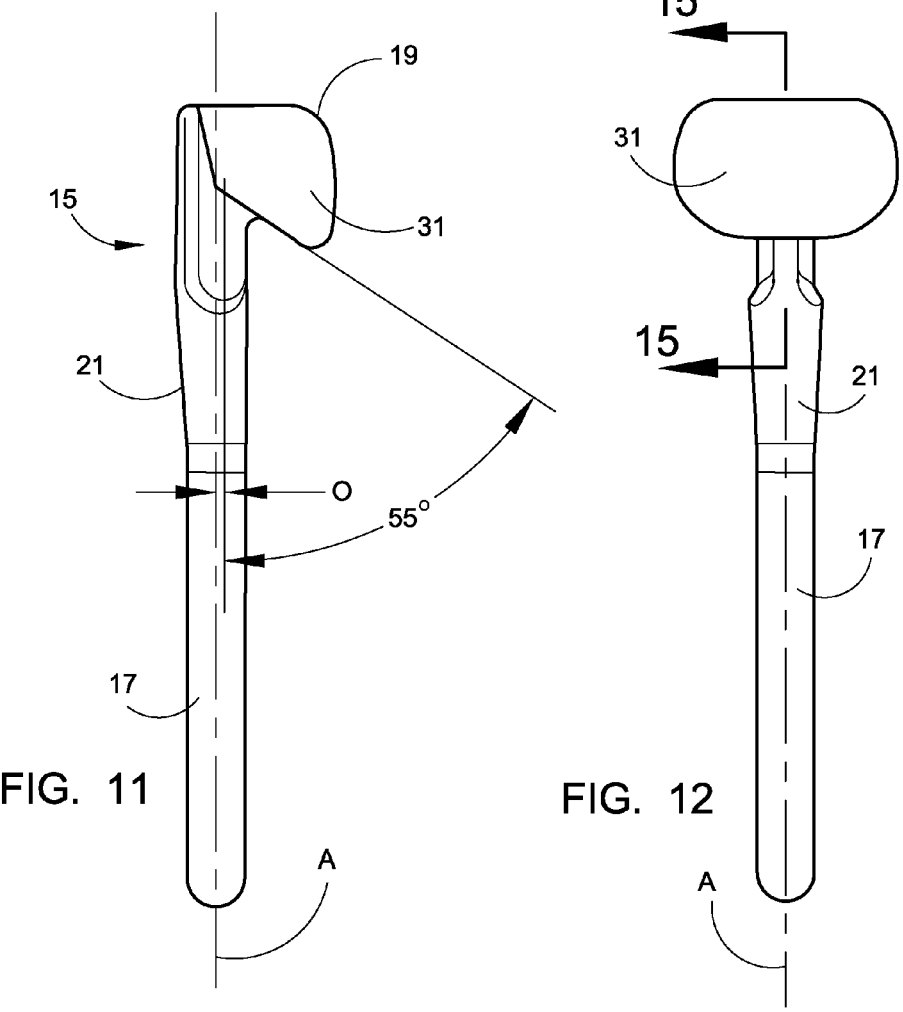
FIG. 11 is a rear or volar view of a prosthesis embodying various features of the invention similar to that shown in FIG. 4.
FIG. 12 is a right side view of the prosthesis of FIG. 11.

FIGS. 4 through 15 show one ulna prosthesis 15 embodying features of the invention which has a head 19 with a convex outer surface 31. It may have a flat top or distal surface 23, or the surface may have a shallow spherical recess 23a in the otherwise flat surface (FIG. 15). The outer surface 31 is preferably curved in two transverse (perpendicular) planes, and it more preferably has a barrel shape where the radius of curvature in a plane parallel to the canal centerline is greater than the radius of curvature in a plane perpendicular thereto. The axis of the barrel shape is offset from the centerline or axis of the medullary canal as shown in FIG. 11 by a distance "O"; such is described hereinafter. The opposite or proximal surface of the head, extending from the region where it surrounds the upper end of the stem like a collar, is constructed to have an arrangement of two flat, planar surfaces. In the preferred arrangement, as best seen in FIGS. 11 and 14, it includes a first distal-extending surface 27 that is angularly offset slightly from the axis A of the stem 17, and a second flat surface 29 that is oblique thereto. The interfacial surface arrangement on the head may also take other shapes that can be similarly mated with the resected surface of the patient's ulna, ranging from that of a cylinder to a flat surface as discussed hereinafter. Edges of the implant are preferably slightly rounded as shown.

Figure 2:
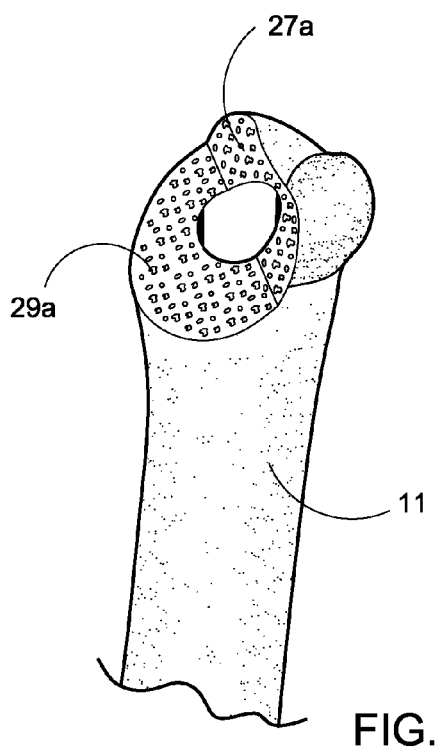
FIG. 2 is a perspective view showing the distal head of a resected ulna.
Figure 3:
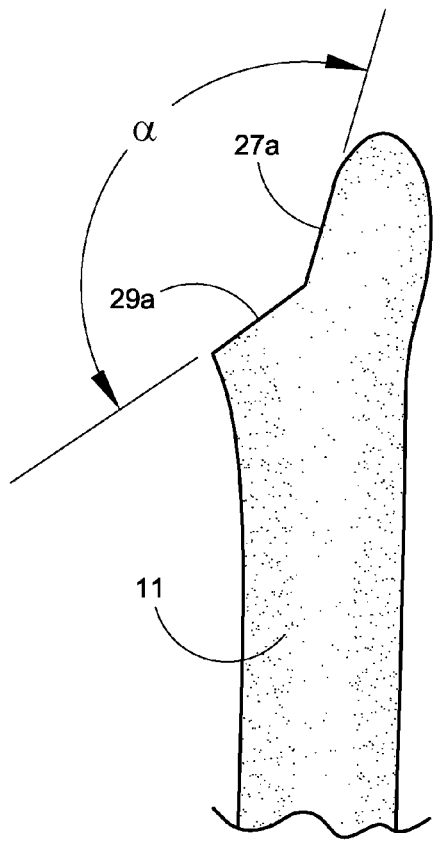
FIG. 3 is a front or dorsal view of the ulna head shown in FIG. 2.
Figure 9:
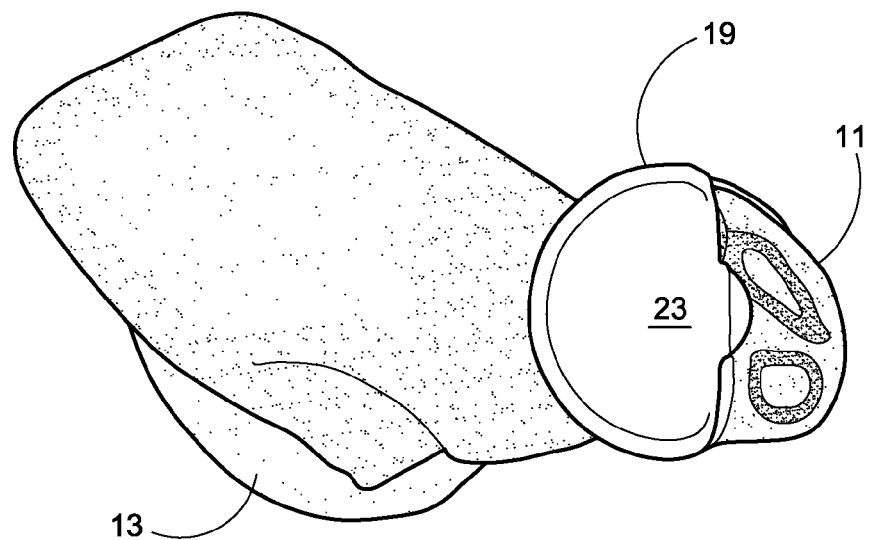
FIG. 9 is a top or distal view of the DRU joint showing the repaired ulna of FIGS. 6-8 and the radius.
Figure 10:
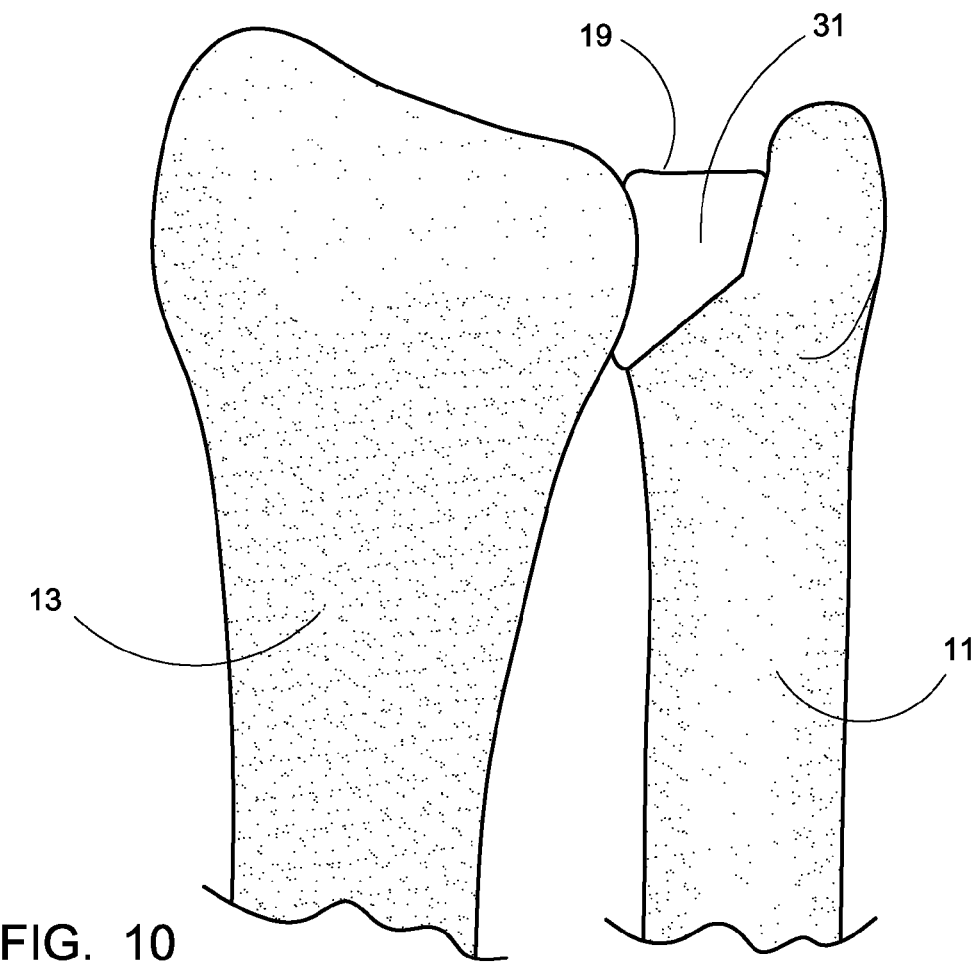
FIG. 10 is a dorsal view of the DRU joint shown in FIG. 9.

To prepare an ulna 11 which is in need of repair to accept this shaped prosthesis 15, the ulna is reamed and resected to open the medullary canal and provide complimentary flat surfaces having the same angular relationship to each other as the surfaces 27 and 29. The surfaces of the resected ulna 11 in FIG. 2 are designated as 27a and 29a. As shown in FIG. 3, the angle of orientation between these two surfaces in this preferred embodiment is indicated as α, and it should be between about 130° and 150°, and preferably between about 135° and 145°, and more preferably about 140° +/−2°. The resection of the ulna is carried out so that the flat surface 27a extends from a line adjacent the ulna styloid to a central line past the centerline axis of the medullary canal. It is preferably aligned at an angle of between about 10° and 15° to the canal centerline. The oblique flat surface 29a meets the surface 27a at this central line on the radius side of the canal centerline. This central line preferably lies in a plane with the centerline of the barrel surface. The flat surface 29a extends at the desired angle a from the flat surface 27a.

As best seen in FIG. 14, the two surfaces 27 and 29 which constitute the stabilizing surface arrangement are similarly aligned at the angle α, i.e. 140°, so that when the prosthesis 15 has been implanted in the reamed and resected ulna shown in FIGS. 2 and 3, it provides an extremely stable fit, with the surfaces of these two pairs of similarly angled surfaces interfacing and abutting each other across their entire surface areas. Of course, the exterior angle between the surfaces 27 and 29 is the complement of α, i.e. 220°.

The placement of the surfaces 27 and 29 on the prosthetic implant relative to the stem in this preferred embodiment is considered to be advantageous in achieving the particularly high stability and strength in such an ulna implant which effect only partial resurfacing and assures the performance desired is achieved. In this respect, the employment of such an exterior angle of between about 210° and 230°, preferably about 220° appears to truly lock the interfacing surfaces together, providing stability in uniting the prosthesis with the resected ulna. Moreover, its location relative to the canal centerline adds to the strength and support that result once the head 19 of the implant is united with the resected head of the ulna 11. Moreover, the location of the angled surface 27a also assists in guiding the prosthesis into the reamed and resected ulna which is seen in FIG. 2.

The preferred double-curved surface 31 of the head 19 provides essentially the entire articular surface for the resurfaced ulna, and it is sized so that it interfaces smoothly with the articular surfaces on the radius. In this respect, the surface 31 is more preferably barrel-shaped, as previously indicated, and the centerline of the barrel is offset slightly toward the radius, by the distance "O", from the centerline of the stem to which it is parallel. The barrel centerline preferably lies in the plane with the central edge at which the flat surfaces 27 and 29 intersect. The preferred relative placement of the surface 31 is such that the point on the barrel surface 31 that is located the furthest from the centerline of the stem will lie in a plane perpendicular to the barrel axis, i.e. the plane of widest diameter, that is located below (i.e. proximally of) the central line of intersection between the surfaces 27 and 29; this alignment provides added stability in the DRUJ having this hemi-reconstruction.

The prosthesis 15 shown in FIG. 11 depicts the head 19 with the centerline of the barrel surface 31 of the head offset by distance "O" from the centerline of the stem. For example, an implant 15 having a head that is 19 mm in diameter for its greatest diameter may be offset by, for example, about 2 mm. Thus, the furthest point on this surface would be 11.5 mm from the centerline of the stem 17 and the medullary canal. Preferably this offset should fall within the range of between about 5% and about 15% of the largest diameter of the barrel surface, i.e. in a plane perpendicular to the axis of the barrel.

The ulnar prosthesis 15 has a stem 17 that may be cylindrical in shape over most of its length, and the total length of the implant should be between about 5 and about 6 times the height of the head, as seen in FIG. 12. Alternatively, when a set of such implants is preferably provided to a surgeon, the stems of the prostheses in the set may be constructed so as to vary slightly in length, with stems of greater diameter in such set having a slightly greater length than those of smaller diameter. The outward taper portion 21 is conical in shape and generally begins in the upper half of the total length of the implant. The ulnar prosthesis is preferably made of a chrome-cobalt alloy or surgical stainless steel as an integral piece; however, it might be made out of other suitable materials as known and used in the orthopedic field and might be made of two pieces, i.e., head and stem that are affixed to each other.

Preferably the ulnar prosthesis 15 is manufactured and distributed as a part of a set in several head and stem sizes to make it possible for the surgeon to choose the best sized prosthesis to file the ulnar head being resurfaced. Head sizes preferably vary from about 14.5 to 19 mm, and stems preferably vary from about 4.3 to 6.4 mm. Manufacture of the implants in two piece construction might be preferred to facilitate the provision of such heads in combination with stems of different diameters. The following Table lists 12 different sizes of prostheses which have been found to provide adequate selection to allow a surgeon to accommodate over 95% of anthropometeric variations without needing to make any substantial compromise.

TABLE

| HEAD DIAMETER (mm) | STEM DIAMETERS (in.) | | |
|---|---|---|---|
| 14.5 | 0.17 | 0.21 | 0.25 |
| 16 | " | " | " |
| 17.5 | " | " | " |
| 19 | " | " | " |

To prepare ulna for repair, the ulna bone is cut so there is only minimal resection of the distal end thereof, mainly in the region facing the radius where articulation primarily occurs. The protruding portion of the distal head and the opposite ulnar surface remain, and they secure the anchoring of the soft tissue components to the bone.

During the operation, the prepared distal ulnar end can be pivoted to facilitate the cut, boring and implantation of the ulnar prosthesis 15 and facilitate the eventual use of a cutting guide. When the ulna surface replacement is made using a prosthesis embodying features of this invention, the ulnocarpal ligaments and the triangular fibrocartilaginous complex (TFCC or the disc) normally are maintained. The passive compressive forces of the DRU joint are thus maintained.

Although the orientation of the distal joint surfaces of the radius and ulna varies somewhat between individuals, a standard orientation in the ulna can be used to provide the resurfaced ulnar portion appropriately oriented relative to the radius. The surgeon first begins using a pointed starter awl at the distal end of the ulna and then reams the medullary canal using boring tools of increasing diameter until he reaches the size stem that he decides the prosthesis 15 should have. The end of the reaming tool in the bored canal then provides a strategically located base to permit the installation of a cutting guide which can be fitted onto a shank portion thereof. Angled cuts are then begun or at least scribed using this guide. The guide and the reaming tool are then removed, and the two cuts can be made free hand to provide the angled planar surfaces 27a and 29a that complement the surfaces 27 and 29 of the ulnar head 19 in the ulna; alternatively the guide can be replaced without the reaming tool to assure accuracy.

Once boring is completed, the prosthesis 15 is inserted so that the stem enters the bored canal, guided by the angled surface 27a in the ulna. The bore is made to about the same size as the diameter of the lower end portion of the stem 17 of the prosthesis to be used, and thus, when the upper, slightly tapered portion 21 of the stem enters the canal during insertion, a tight press fit is accomplished. Further stabilization results when the implant is fully inserted so as to seat it with the surfaces 27 and 29 in abutting contact with the surfaces 27a and 29a of the resected ulna. The combination of the stem in the bored medullary canal and the abutting pairs of planar surfaces which are oriented so that the surfaces are angularly offset in both directions from the centerline of the stem/medullary canal provides extreme stability in the ultimate implant. Likewise, the location of the barrel-shaped articular surface is such that it smoothly interfaces with the corresponding articular surface of the radius along substantially its entire longitudinal length.

As previously indicated, the prosthetic implant is not necessarily limited to having the two-surface angled stabilizing surface arrangement illustrated in FIGS. 4-15, although that arrangement is most preferred. Illustrated in FIGS. 16 and 17 is one alternative embodiment of an implant 41 embodying various features of the invention which is similar in construction to the implant 15 except that, instead of utilizing a pair of angled surfaces 27 and 29, the head 43 of the implant 41, which surmounts a stem 45 of similar construction to the stem 17, is formed with a stabilizing surface 47 that is a section of a right circular cylinder. The radius of the cylinder is preferably between about 300% and 500% of the radius of the articular surface of the head 43, and more preferably, between about 350% and about 450% thereof. The radius is depicted as length R, and the location of the center of curvature (c) of the cylindrical stabilizing surface is preferably at about a 45° angle to the canal centerline, i.e. the centerline of the stem from the point where that centerline intersects the plane perpendicular thereto that constitute the midplane of the head 43, which is marked MP in FIG. 16. As viewed in FIG. 16, the center of curvature (c) is located above the flat distal surface 49 of the head 43, and it is preferably spaced above the MP at a distance equal to between about 2 and 2½ times the height of the head 43. With this orientation, as can be seen in FIGS. 16 and 17, the stabilizing cylindrical surface extends past the canal centerline at its distal end, but it preferably stops just short of a point that would lie on the far surface of an extended projection of the stem, as best seen in FIG. 17. The distal surface 49 is preferably formed with a central shallow recess 49a.

The articular surface of the head 43 is that of a modified barrel construction being curved in the planes perpendicular to the canal centerline as a result of having a central cylindrical portion 51 and an upper section 53 and lower section 55 which are portions of the surface of a torus. Again, there is preferably an offset, as described hereinbefore, between the axis of rotation of the central cylindrical section 51 and the axis of the stem 45, with the surface 51 axis being offset toward the radius by the previously described distance O.

When implanting the implant 41, a surgeon will have the choice of resecting the ulna to create a complementary cylindrical surface or, alternatively, to make the same pair of intersecting cuts as described before. In the latter instance, when the stem 45 is fully inserted into the reamed intermedullary canal, the stabilizing cylindrical surface 47 will abut and contact these resected surfaces of the ulna along two parallel lines and provide a stable seating.

Illustrated in FIGS. 18 and 19 is another alternative embodiment of an implant 61 embodying various features of the invention which is similar in construction to the implant 15 in that it also utilizes a pair of angled surfaces 63, 65 on the proximal surface of its head 67, which surmounts a stem 69 of similar construction to the stem 17. Its articular surface 71 is a section of a sphere. The diameter of the sphere is preferably about that of the head diameters set forth in the TABLE. The spherical surface 71 of the head 67 preferably has its center of curvature located along a line parallel to the axis of the stem which is offset toward the radius by the previously described distance O. The distal region of the head 61 may be a continuation of the spherical articular surface 71 except for a central shallow recess 73. With this orientation, as can be seen in FIGS. 18 and 19, edge portions of the spherical surface extend past the canal centerline at its distal end but preferably stop just short of what would constitute an extended projection of the stem. Sharp edges are generally rounded as shown by shading. When implanting the implant 61, the surgeon will resect the ulna to make the same pair of intersecting cuts as described before.

As a further alternative construction, an implant of this type can be created that uses just a single flat surface as the stabilizing surface along which the head will interface with the resected distal end of the ulna. Such an alternative embodiment of a prosthetic implant would resemble that shown in FIGS. 11 and 14 where the angle α is 180°. The flat surface is preferably oriented at an angle between about 25° and about 45° to the centerline of the stem instead of the 55° angle shown in FIG. 11. More preferably, the orientation is between about 30° and about 40° and most preferably between about 33° and about 37°. Although the head is preferably proportioned and the stabilizing surface located so that, when the ulna is resected, the plane of resection might extend further past the centerline of the medullary canal than that shown in FIGS. 2 and 3, it should preferably terminate short of the distal tips of the two lobes of the ulnar head shown in FIGS. 2 and 3. Such a construction for the implant head would slightly simplify the surgeon's resection of the distal end of the ulna.

Although the invention has been described with respect to certain preferred embodiments, various changes and modifications as would be obvious to one having the ordinary skill in this art may be made without departing from the scope of this invention which is defined solely by the appended claims. For example, a set of 12 prostheses for provision to a surgeon could include, for example, only two different sized stems, with subsets of prostheses of the same head and stem sizes being constructed where the head is offset by different distances from the centerline of the stem. Such feature allows the surgeon to make a choice not only to provide the best fitting, but also to effect the most desirable tension of soft tissue. By proper selection of both the head diameter and the relative head center location, the soft tissues which cross the DRU joint are allowed to maintain nearly constant tension throughout the pronation-supination range of motion. Although the articular surface of the head may have the double-curved barrel construction, modified barrel construction or spherical construction, other generally similar surfaces, e.g. ellipsoidal, may also be used. The disclosures of the aforementioned U.S. patents and published application are expressly incorporated herein by reference.

Particular features of the invention are emphasized in the claims that follow.

The invention claimed is:

1. A prosthetic implant for partial replacement of the ulnar head at the distal radioulnar joint (DRUJ) without disturbing attachment of ulnar carpal ligaments and the triangular fibrocartilaginous complex (TFCC), which implant comprises
    an elongated stem which is of circular cross section and has a centerline and which is designed to fit within a bore created in a patient's ulna and
    a head which surmounts said stem and is proportioned to replace the radial-articulating surface of the distal ulna and only a portion of the ulnar head, which portion extends past the centerline of the medullary canal when implanted,
    said implant head having a double-curved lateral articular surface and a stabilizing surface from which said stem extends, which stabilizing surface includes a distal planar surface section and a proximal planar surface section, which planar surface sections are aligned at an interior obtuse angle to each other between about 130° and 150° so as to stably interface across their entire surface areas with complementary similarly angled planar surfaces of the resected ulna of the DRUJ when implanted, said distal and proximal planar surface sections intersecting at a line of intersection which lies in a plane perpendicular to said centerline of said stem, said proximal planar surface section being aligned at an angle of about 55° to said centerline, and said distal planar surface section adapted to interface with the resected planar complementary surface of the ulna which surface extends past said centerline of said medullary canal when implanted.

2. The implant of claim 1 wherein said double-curved articular surface is barrel-shaped.

3. The implant of claim 2 wherein said barrel-shaped articular surface has a centerline that is parallel to said centerline of said stem and offset therefrom in the direction toward the radius when implanted.

4. The implant according to claim 3 wherein said line of intersection intersects and is perpendicular to said centerline of said stem.

5. The implant of claim 4 wherein said double-curved articular surface is barrel-shaped and has its diameter of greatest dimension in a plane located proximal of said line of intersection of said two planar surfaces.

6. The implant of claim 1 wherein said head is integral with said stem.

7. The implant according to claim 1 wherein said interior obtuse angle is about 140° ±2°.

8. A prosthetic implant for partial replacement of the ulnar head at the distal radioulnar joint (DRUJ), which implant comprises
    an elongated stem which is of circular cross section and has a centerline, and which is designed to fit within a bore created in a patient's ulna and
    a head which has a barrel-shaped double-curved lateral articular surface and distal and proximal planar stabilizing surfaces located at an interior obtuse angle to each other of between about 130° and 150°, said barrel-shaped articular surface having a centerline that is parallel to said centerline of said stem and is offset therefrom in the direction toward the radius when implanted,
    said proximal planar surface being aligned at an angle of about 55° to said centerline of said stem, said distal planar surface being aligned at an angle of between about 10° and 15° with said centerline of said barrel-shaped articular surface, and said planar surfaces intersecting at a line of intersection which lies in a plane perpendicular to said centerline of said stem and substantially intersecting said centerline of said stem,
    whereby the implanted prosthesis provides for stable replacement of the radial-articulating surface of the distal ulna without disturbing attachment of ulnar carpal ligaments and the triangular fibrocartilaginous complex (TFCC).

9. The implant of claim 8 wherein said barrel-shaped articular surface has its diameter of greatest dimension in a plane located proximal of said line of intersection at which said distal and proximal planar surfaces intersect.

10. A prosthetic implant for partial replacement of the ulnar head at the distal radioulnar joint (DRUJ) without disturbing attachment of ulnar carpal ligaments and the triangular fibrocartilaginous complex (TFCC), which implant comprises an elongated stem which is of circular cross section and has a centerline and which is designed to fit within a bore created in a patient's ulna and an integral head which surmounts said stem and is proportioned to replace the radial-articulating surface of the distal ulna and only a portion of the ulnar head but which portion extends past the centerline of the medullary canal when implanted, said implant head having a double-curved lateral articular surface that is barrel-shaped and a stabilizing surface from which said stem extends, said stabilizing surface including a distal planar surface section and a proximal planar surface section, which planar surface sections are aligned at an interior obtuse angle to each other between about 130° and 150° and will stably interface across their entire continuous surface areas with complementary similarly-angled planar surfaces of the resected ulna of the DRUJ when implanted, said distal and proximal planar surface sections intersecting at a line of intersection which lies in a plane perpendicular to said centerline of said stem, said proximal planar surface section being aligned at an angle of about 55° to said centerline, and said distal planar surface being aligned at an angle of about 10° to 15° to said centerline of the canal which it extends past when implanted.

* * * * *